(12) United States Patent
Busolli et al.

(10) Patent No.: US 9,562,050 B2
(45) Date of Patent: Feb. 7, 2017

(54) CRYSTALLINE FORMS OF PEMETREXED DIACID AND PROCESSES FOR THE PREPARATION THEREOF

(71) Applicant: Sicor Inc., Irvine, CA (US)

(72) Inventors: Jonathan Busolli, Carisio (IT); Nicola Diulgheroff, Turin (IT); Csilla Nemethne Racz, Tiszavasvari (HU); Moran Pirkes, Turin (IT); Alessandro Pontiroli, Milan (IT); Marco Villa, Milan (IT); Judith Aronhime, Rehovot (IL)

(73) Assignee: Sicor, Inc., Irvine, CA (US)

( * ) Notice: Subject to any disclaimer, the term of this patent is extended or adjusted under 35 U.S.C. 154(b) by 0 days.

(21) Appl. No.: 14/855,818

(22) Filed: Sep. 16, 2015

(65) Prior Publication Data

US 2016/0002253 A1 Jan. 7, 2016

Related U.S. Application Data

(62) Division of application No. 13/070,432, filed on Mar. 23, 2011, now Pat. No. 9,156,841, which is a division of application No. 11/893,212, filed on Aug. 14, 2007, now Pat. No. 8,088,919.

(60) Provisional application No. 60/837,303, filed on Aug. 14, 2006, provisional application No. 60/837,637, filed on Aug. 15, 2006, provisional application No. 60/839,551, filed on Aug. 22, 2006, provisional application No. 60/845,031, filed on Sep. 14, 2006, provisional application No. 60/855,139, filed on Oct. 30, 2006, provisional application No. 60/860,557, filed on Nov. 21, 2006, provisional application No. 60/860,554, filed on Nov. 21, 2006, provisional application No. 60/880,179, filed on Jan. 11, 2007, provisional application No. 60/880,178, filed on Jan. 11, 2007, provisional application No. 60/899,928, filed on Feb. 6, 2007, provisional application No. 60/936,553, filed on Jun. 20, 2007, provisional application No. 60/958,326, filed on Jul. 2, 2007, provisional application No. 60/958,213, filed on Jul. 3, 2007, provisional application No. 60/958,413, filed on Jul. 5, 2007.

(51) Int. Cl.
C07D 487/04 (2006.01)

(52) U.S. Cl.
CPC ......... *C07D 487/04* (2013.01); *C07B 2200/13* (2013.01)

(58) Field of Classification Search
CPC .. A61K 31/519; C07D 487/04; C07B 2200/13
USPC ........................................ 544/280; 514/265.1
See application file for complete search history.

(56) References Cited

U.S. PATENT DOCUMENTS

| | | | |
|---|---|---|---|
| 5,248,775 | A | 9/1993 | Taylor et al. |
| 5,344,932 | A | 9/1994 | Taylor |
| 5,416,211 | A | 5/1995 | Barnett et al. |
| 6,262,262 | B1 | 7/2001 | Kjell |
| 7,138,521 | B2 | 11/2006 | Chelius et al. |
| 2003/0216416 | A1 | 11/2003 | Chelius et al. |

FOREIGN PATENT DOCUMENTS

| | | |
|---|---|---|
| EP | 0 432 677 | 6/1991 |
| EP | 0 434 426 | 6/1991 |
| WO | WO 01/14379 | 3/2001 |
| WO | WO 2008/124485 | 10/2008 |
| WO | WO 2010/031357 | 3/2010 |

OTHER PUBLICATIONS

Bhattacharya et al. (Brittain, ed. Polymorphism in Pharmaceutical Solids, 2009, p. 334.
Notebook page and diffractogram of Applicants' experimental results for a $2^{nd}$ repetition of example 7 in U.S. Pat. No. 6,262,262, Feb. 2009.
Applicants' Experimental Results: Repetition of Example 7 of U.S. Pat. No. 6,262,262 and Preparation of 6 of U.S. Pat. No. 5,416,211 date received Aug. 14, 2007 in parent application.
Taylor J. Med. Chem., 35 pp. 4450-4454, 1992,.
Physicians' Desk Reference, 1722-1728 ($60^{th}$ ed. 2006).
Barnett, Charles, et al., "A Practical Synthesis of Multitargeted Antifolate LY231514," Organic Process Research & Development, 3(3): 184-188, 1999.
U.S. Pharmacopeia, 387-389, $30^{th}$ ed., 2007.
Kjell, Douglas P., et al., "Determination of the Source of the N-Methyl Impurity in the Synthesis of Pemetrexed Disodium Heptahydrate," Organic Process Research and Development, 9(6); 738-742 (2005).
International Conference on Harmonisation of Technical Requirements for Registration of Pharmaceuticals for Human Use, ICH Harmonized tripartite Guideline: Good for Manufacturing Practice Guide for Active Pharmaceutical Ingredients Q7 (Current Step 4 Version, Nov. 10, 2000)(available at http://www.ich.org/LOB/media/MEDIA433.pdf, last visited Dec. 21, 2007).

*Primary Examiner* — Susanna Moore
(74) *Attorney, Agent, or Firm* — Baker & Hostetler LLP

(57) ABSTRACT

Provided are crystalline forms of N-[4-[2-(2-amino-4,7-dihydro-4-oxo-1H-pyrrolo[2,3-d]pyrimidin-5-yl)ethyl]benzoyl]-L-glutamic acid, pemetrexed diacid, and processes for the preparation thereof.

4 Claims, 4 Drawing Sheets

Fig.1: An X-ray powder diffraction pattern of crystalline pemetrexed diacid characterized by an X-ray powder diffraction pattern with peaks at about 10.0, 10.3, 22.0 and 25.7 degrees two-theta ± 0.2 degrees two-theta

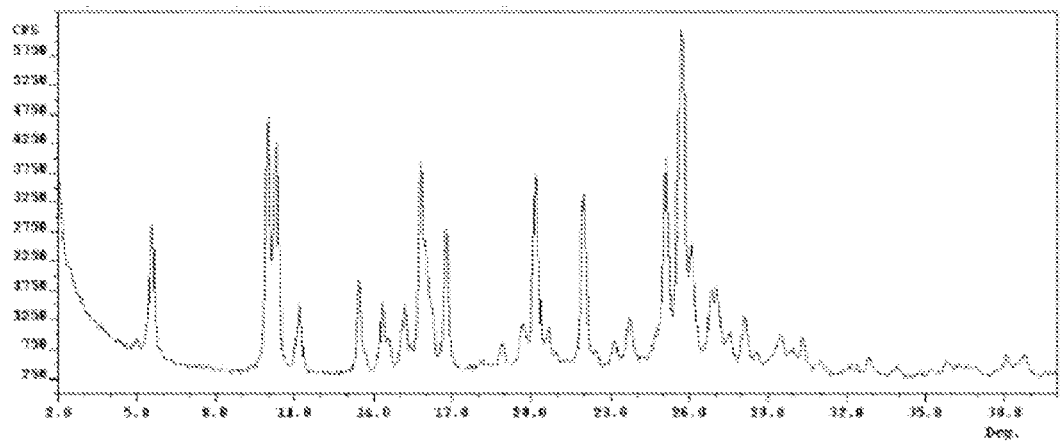

Fig.2: An X-ray powder diffraction pattern of crystalline pemetrexed diacid characterized by an X-ray powder diffraction pattern with peaks at about 5.7, 12.2, 17.2 and 18.4 degrees two-theta ± 0.2 degrees two-theta.

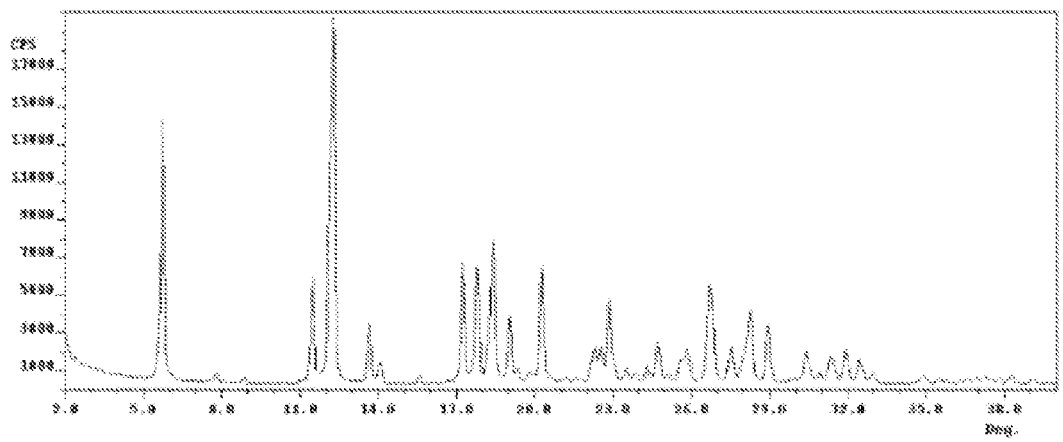

Fig.3: An X-ray powder diffraction pattern of crystalline pemetrexed diacid characterized by an X-ray powder diffraction pattern with peaks at about 5.8, 12.4, 18.6 and 24.6 degrees two-theta ± 0.2 degrees two-theta.

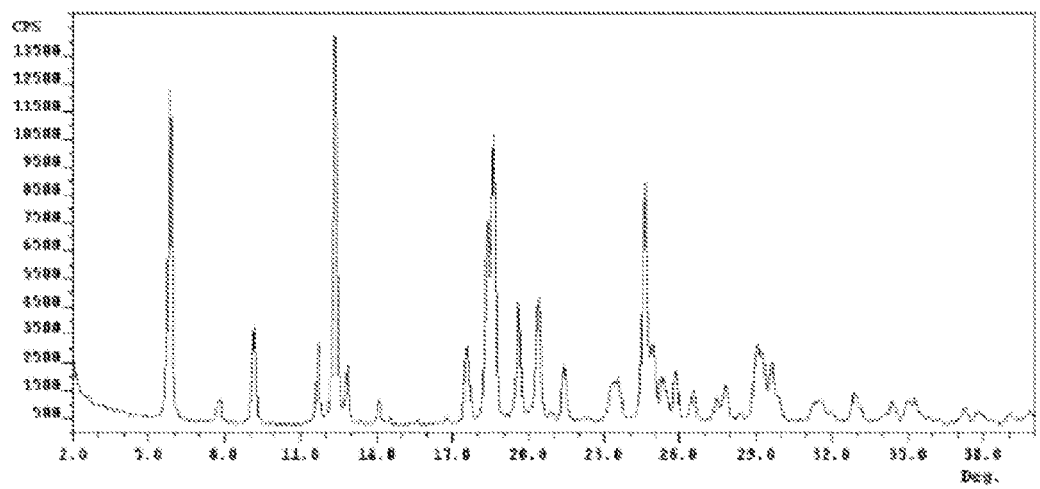

Fig.4:. An X-ray powder diffraction pattern of crystalline pemetrexed diacid characterized by an X-ray powder diffraction pattern with peaks at about 6.2, 10.7, 12.0 and 18.9 degrees two-theta ± 0.2 degrees two-theta.

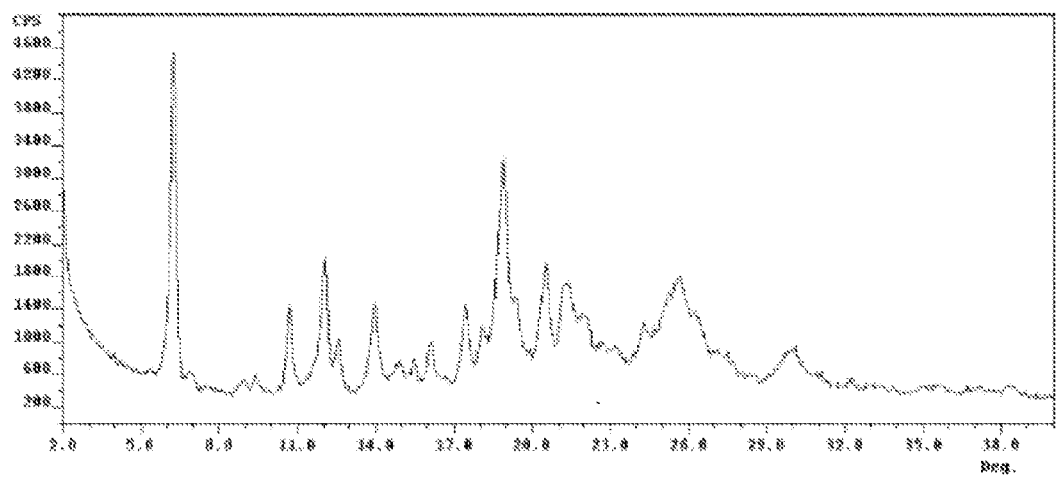

Fig.5: An X-ray powder diffraction pattern of crystalline pemetrexed diacid characterized by an X-ray powder diffraction pattern with peaks at about 9.0, 16.2, 18.1 and 26.9 degrees two-theta ± 0.2 degrees two-theta

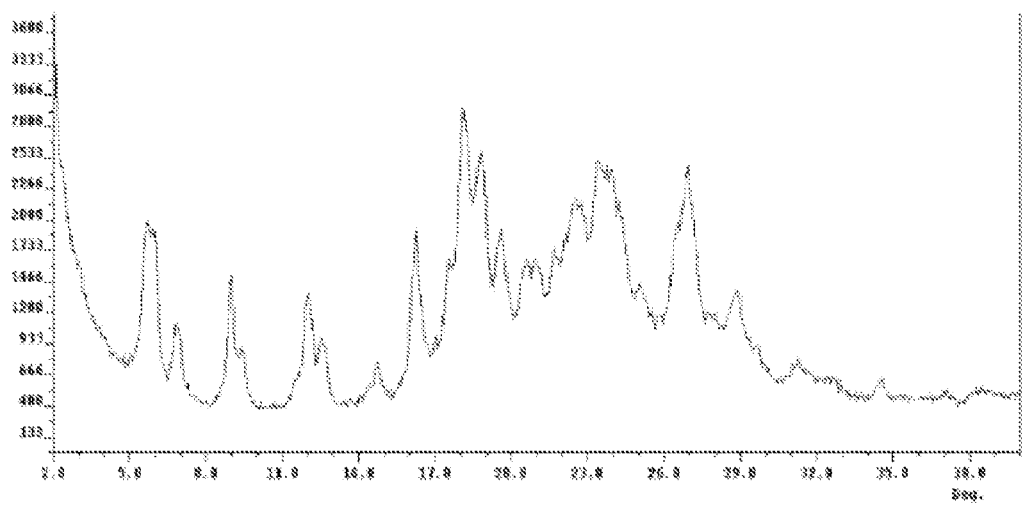

Fig.6: An X-ray powder diffraction pattern of crystalline pemetrexed diacid characterized by an X-ray powder diffraction pattern with peaks at about 7.7, 9.2, 16.7, and 27.4 degrees two-theta ± 0.2 degrees two-theta.

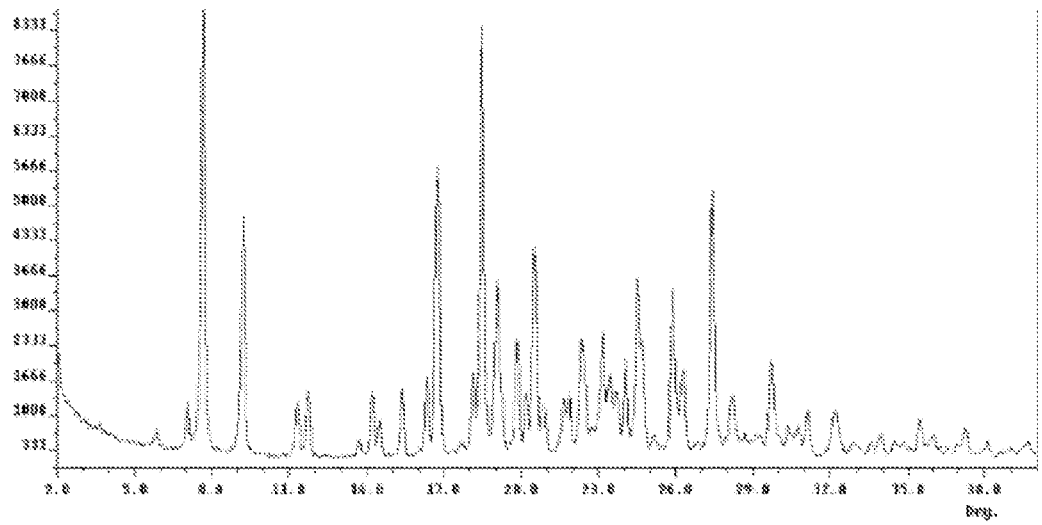

Fig.7: An X-ray powder diffraction pattern of crystalline pemetrexed diacid characterized by an X-ray powder diffraction pattern with peaks at about 6.8, 11.9, 15.5 and 17.9 degrees two-theta ± 0.2 degrees two-theta.

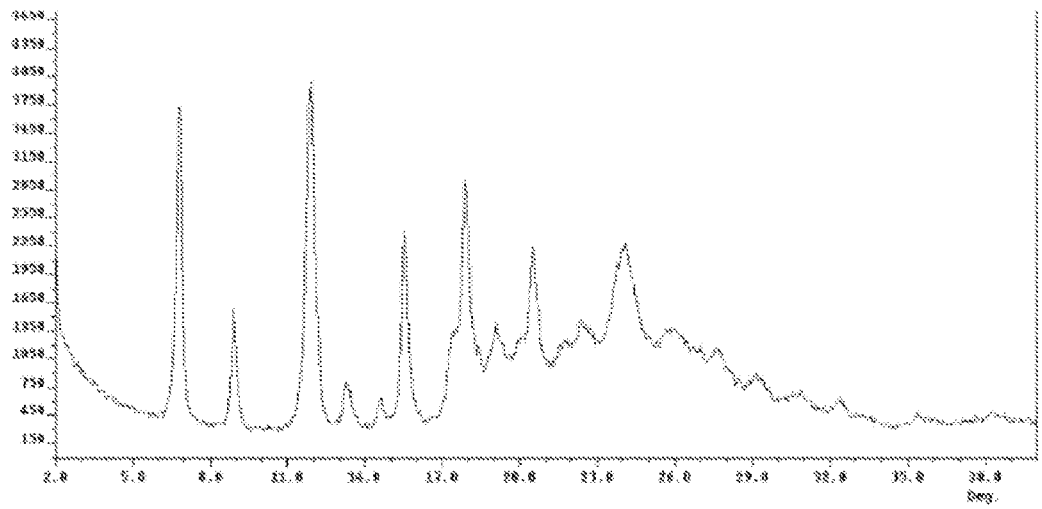

Fig. 8: An X-ray powder diffraction pattern of crystalline pemetrexed diacid characterized by an X-ray powder diffraction pattern with peaks at about 5.7, 12.2, 17.2 and 18.4 degrees two-theta ± 0.2 degrees two-theta obtained in example 12.

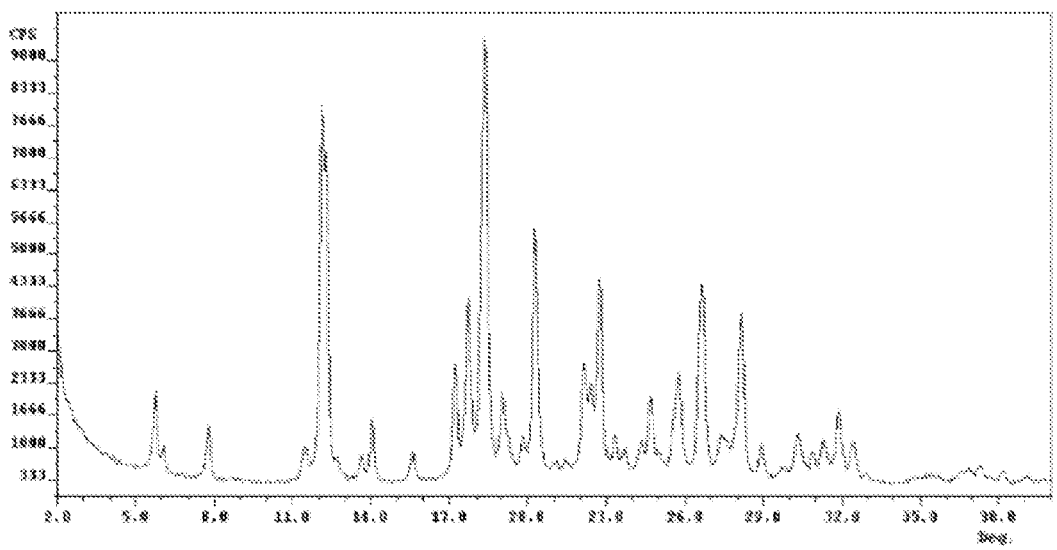

CRYSTALLINE FORMS OF PEMETREXED DIACID AND PROCESSES FOR THE PREPARATION THEREOF

CROSS REFERENCE TO RELATED APPLICATIONS

This application is a divisional of application Ser. No. 13/070,432, filed Mar. 23, 2011, now U.S. Pat. No. 9,156, 841, which is a divisional of application Ser. No. 11/893, 212, filed Aug. 14, 2007, now U.S. Pat. No. 8,088,919, which claims the benefit of U.S. provisional application Ser. Nos. 60/837,303, filed Aug. 14, 2006; 60/837,637, filed Aug. 15, 2006; 60/860,557, filed Nov. 21, 2006; 60/860,554, filed Nov. 21, 2006; 60/880,178, filed Jan. 11, 2007; 60/958,213, filed Jul. 3, 2007; 60/839,551, filed Aug. 22, 2006; 60/845, 031, filed Sep. 14, 2006; 60/899,928, filed Feb. 6, 2007; 60/936,553, filed Jun. 20, 2007; 60/958,413, filed Jul. 5, 2007; 60/847,291, filed Sep. 25, 2006; 60/855,139, filed Oct. 30, 2006; 60/880,179, filed Jan. 11, 2007; and 60/958,326, filed Jul. 2, 2007, hereby incorporated by reference.

FIELD OF THE INVENTION

The invention encompasses crystalline forms of N-[4-[2-(2-amino-4,7-dihydro-4-oxo-1H-pyrrolo[2,3-d]pyrimidin-5-yl)ethyl]benzoyl]-L-glutamic acid, pemetrexed diacid, and processes for the preparation thereof.

BACKGROUND OF THE INVENTION

Compounds known to have antifolate activity are well recognized as chemotherapeutic agents for the treatment of cancer. In particular, compounds in the folic acid family have various activities at the enzymatic level as they inhibit such enzymes as dehydrofolate reductase, folate polyglutamate synthetase, glycinamide ribonucleotide formyltransferase and thymidylate synthetase.

European publication No. 0434426 ("EP '426") discloses a class of 4-hydroxypyrrolo[2,3-d]pyrimidine-L-glutamic acid derivatives, and states that these compounds have antifolate activity and anti-tumor effect. See EP '426, p. 2, 11. 33-56. Among them are hydrate crystalline forms of disodium pemetrexed.

Pemetrexed disodium salt heptahydrate is marketed by Eli Lilly and Company under the trade name ALIMTA® as a sterile lyophilized powder for intravenous administration. This member of the folic acid family has been approved for treatment of malignant pleural mesothelioma and for second-line treatment of non small cell lung cancer. See *Physicians' Desk Reference*, 60th ed., pp. 1722-1728 (2006).

International PCT publication WO 01/14379 discloses hydrate crystalline disodium pemetrexed.

The preparation of the commercial lyophilized or formulated lyophilized pemetrexed disodium is disclosed in U.S. Pat. No. 7,138,521. This pemetrexed disodium is prepared from N-[4-[2-(2-Amino-4,7-dihydro-4-oxo-3H-pyrrolo[2,3-d]pyrimidin-5-yl)ethyl]benzoyl]L-glutamic acid diethyl-ester p-toluenesulfonic acid salt, which is saponified at a pH of between 2.5 to 3.5 to give N-[4-[2(2-amino-4,7-dihydro-4-oxo-1H-pyrrolo[2,3-d]pyrimidin-5-yl)ethyl]benzoyl]-L-glutamic acid ("pemetrexed diacid"), of the following Formula II:

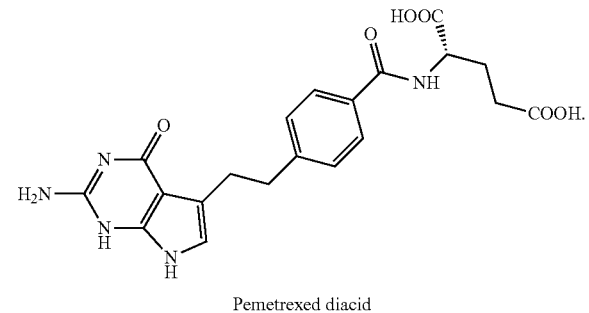 [SMILES: Nc1nc(=O)c2c(CCc3ccc(C(=O)N[C@@H](CCC(=O)O)C(=O)O)cc3)c[nH]c2[nH]1]

Pemetrexed diacid

The pemetrexed diacid is isolated as a wet cake and then combined with 2 to 3 equivalents of sodium hydroxide at a pH of between 7 and 9. The resulting pemetrexed disodium heptahydrate is then isolated from the reaction mixture by precipitation using acetone. The isolated pemetrexed disodium heptahydrate is then used to prepare the pharmaceutical composition.

Pemetrexed diacid and its preparation is believed to have been described for the first time in U.S. Pat. No. 5,344,932.

Formation and isolation of N-[4-[2-(2-amino-4,7-dihydro-4-oxo-3H-pyrrolo[2,3-d]pyrimidin-5-yl)ethyl]benzoyl]-L-glutamic acid from a mixture of water and ethanol having a pH of 2.5-3.5 is disclosed in U.S. Pat. No. 7,138, 521. A similar isolation is disclosed in C. J. Barnett, et al., "A Practical Synthesis of Multitargeted Antifolate LY231514," *Organic Process Research & Development*, 3(3): 184-188 (1999).

Formation and isolation of N-[4-[2-(2-amino-4,7-dihydro-4-oxo-3H-pyrrolo[2,3-d]pyrimidin-5-yl)ethyl]benzoyl]-L-glutamic acid from an aqueous solution having a pH of 5 is disclosed in U.S. Pat. No. 5,416,211.

Formation and isolation of pemetrexed diacid from an aqueous solution of the p-toluenesulfonic acid salt of the corresponding dialkyl ester compound by addition of sodium hydroxide and adjusting the pH to 2.8-3.1 is disclosed in U.S. Pat. No. 6,262,262.

The occurrence of different crystal forms (polymorphism) is a property of some molecules and molecular complexes. A single molecule may give rise to a variety of solids having distinct physical properties like melting point, X-ray diffraction pattern, infrared absorption fingerprint and NMR spectrum. The differences in the physical properties of polymorphs result from the orientation and intermolecular interactions of adjacent molecules (complexes) in the bulk solid.

Accordingly, polymorphs are distinct solids sharing the same molecular formula yet having distinct advantageous and/or disadvantageous physical properties compared to other forms in the polymorph family. One of the most important physical properties of pharmaceutical polymorphs is their solubility in aqueous solution, which may influence the bioavailability of the drug.

These practical physical characteristics are influenced by the conformation and orientation of molecules in the unit cell, which defines a particular polymorphic form of a substance that can be identified unequivocally by X-ray spectroscopy. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by solid state $^{13}C$ NMR spectrometry and infrared spectroscopy.

The discovery of new polymorphic forms of pemetrexed diacid provides a new opportunity to improve the performance of the synthesis of the active pharmaceutical ingredient (API), pemetrexed disodium, by producing crystalline forms of pemetrexed diacid having improved characteristics, such as flowability, and solubility. Thus, there is a need in the art for polymorphic forms of pemetrexed diacid.

SUMMARY OF THE INVENTION

In one embodiment, the invention encompasses crystalline pemetrexed diacid characterized by data selected from the group consisting of: an X-ray powder diffraction ("PXRD") pattern with peaks at about 10.0, 10.3, 22.0 and 25.7 degrees two-theta±0.2 degrees two-theta, and a PXRD pattern as depicted in FIG. 1.

In another embodiment, the invention encompasses crystalline pemetrexed diacid characterized by data selected from the group consisting of: a PXRD pattern having peaks at about 5.7, 12.2, 17.2 and 18.4 degrees two-theta±0.2 degrees two-theta; and a PXRD pattern as depicted in FIG. 2.

In another embodiment, the invention encompasses a process for preparing the above crystalline pemetrexed diacid. The process comprises providing a suspension of pemetrexed diacid in an aqueous solvent having a pH of about 3, and adjusting the pH of the suspension to about 4.5.

In yet another embodiment, the invention encompasses crystalline pemetrexed diacid characterized by data selected from the group consisting of: a PXRD pattern having peaks at about 5.8, 12.4, 18.6 and 24.6 degrees two-theta±0.2 degrees two-theta; and a PXRD pattern as depicted in FIG. 3.

In another embodiment, the invention encompasses crystalline pemetrexed diacid characterized by data selected from the group consisting of: a PXRD pattern having peaks at About 6.2, 10.7, 12.0 and 18.9 degrees two-theta±0.2 degrees two-theta; and a PXRD pattern as depicted in FIG. 4.

In yet another embodiment, the invention encompasses a process for preparing the above crystalline pemetrexed diacid. The process comprises crystallizing pemetrexed diacid from a mixture comprising DMF as a solvent and a mixture of water and methanol as an anti-solvent.

In one embodiment, the invention encompasses crystalline pemetrexed diacid characterized by data selected from the group consisting of: a PXRD pattern having peaks at about 9.0, 16.2, 18.1 and 26.9 degrees two-theta±0.2 degrees two-theta; and a PXRD pattern as depicted in FIG. 5.

In yet another embodiment, the invention encompasses crystalline pemetrexed diacid characterized by data selected from the group consisting of: a PXRD pattern having peaks at about 7.7, 9.2, 16.7 and 27.4 degrees two-theta±0.2 degrees two-theta; and a PXRD pattern as depicted in FIG. 6.

In one embodiment, the invention encompasses a process for preparing the above crystalline pemetrexed diacid. The process comprises admixing N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic acid salt of the following formula

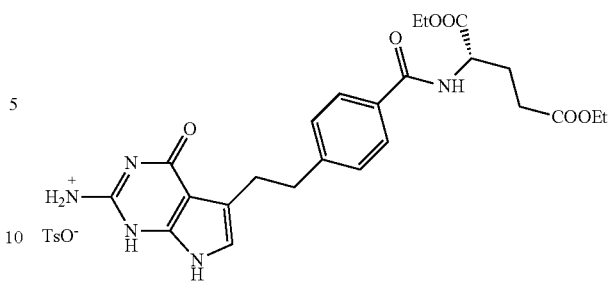

and at least one base to obtain a solution, and adding the solution to an acid to obtain a suspension comprising the said crystalline pemetrexed diacid.

In another embodiment, the invention encompasses crystalline pemetrexed diacid characterized by data selected from the group consisting of: a PXRD pattern having peaks at about 6.8, 11.9, 15.5 and 17.9 degrees two-theta±0.2 degrees two-theta; and a PXRD pattern as depicted in FIG. 7.

In yet another embodiment, the invention encompasses a process for preparing a pharmaceutically acceptable salt of pemetrexed diacid comprising preparing any of the above crystalline pemetrexed diacid by the processes of the invention, and converting them to the pharmaceutically acceptable salt of pemetrexed diacid.

In one embodiment, the invention encompasses a process for preparing a lyophilized form of a pharmaceutically acceptable salt of pemetrexed comprising preparing any of the above crystalline pemetrexed diacid by the processes of the invention, and transforming them to the lyophilized pharmaceutically acceptable salt of pemetrexed. Preferably, the pharmaceutically acceptable salt is pemetrexed disodium.

BRIEF DESCRIPTION OF THE DRAWINGS

FIG. 1. illustrates an X-ray powder diffraction pattern of crystalline pemetrexed diacid characterized by an X-ray powder diffraction pattern with peaks at about 10.0, 10.3, 22.0 and 25.7 degrees two-theta±0.2 degrees two-theta.

FIG. 2. illustrates an X-ray powder diffraction pattern of crystalline pemetrexed diacid characterized by an X-ray powder diffraction pattern with peaks at about 5.7, 12.2, 17.2 and 18.4 degrees two-theta±0.2 degrees two-theta.

FIG. 3. illustrates an X-ray powder diffraction pattern of crystalline pemetrexed diacid characterized by an X-ray powder diffraction pattern with peaks at about 5.8, 12.4, 18.6 and 24.6 degrees two-theta±0.2 degrees two-theta.

FIG. 4. illustrates an X-ray powder diffraction pattern of crystalline pemetrexed diacid characterized by an X-ray powder diffraction pattern with peaks at about 6.2, 10.7, 12.0 and 18.9 degrees two-theta±0.2 degrees two-theta.

FIG. 5. illustrates an X-ray powder diffraction pattern of crystalline pemetrexed diacid characterized by an X-ray powder diffraction pattern with peaks at about 9.0, 16.2, 18.1 and 26.9 degrees two-theta±0.2 degrees two-theta.

FIG. 6. illustrates an X-ray powder diffraction pattern of crystalline pemetrexed diacid characterized by an X-ray powder diffraction pattern with peaks at about 7.7, 9.2, 16.7, and 27.4 degrees two-theta±0.2 degrees two-theta.

FIG. 7. illustrates an X-ray powder diffraction pattern of crystalline pemetrexed diacid characterized by an X-ray powder diffraction pattern with peaks at about 6.8, 11.9, 15.5 and 17.9 degrees two-theta±0.2 degrees two-theta.

FIG. 8 illustrates an X-ray powder diffraction pattern of crystalline pemetrexed diacid characterized by an X-ray powder diffraction pattern with peaks at about 5.7, 12.2, 17.2 and 18.4 degrees two-theta±0.2 degrees two-theta obtained in example 12.

DETAILED DESCRIPTION OF THE INVENTION

The invention addresses a need in the art by providing crystalline forms of pemetrexed diacid, as well as methods for their preparation.

The time periods described herein are time periods suitable for laboratory-scale preparations. One of ordinary skill in the art understands that suitable time periods will vary based upon the amounts of reagents present, and can adjust the time periods accordingly.

The invention encompasses crystalline pemetrexed diacid characterized by data selected from the group consisting of: an X-ray powder diffraction ("PXRD") pattern having peaks at about 10.0, 10.3, 22.0 and 25.7 degrees two-theta±0.2 degrees two-theta; and a PXRD pattern as depicted in FIG. 1. This crystalline pemetrexed diacid can be designated as Form A.

One of ordinary skill in the art is aware that there is a certain amount of experimental error inherent in powder X-ray diffraction ("PXRD") techniques. See, e.g., U.S. PHARMACOPEIA, 387-89 (30th ed. 2007), hereby incorporated by reference. As to individual peaks, peak positions are reported over a range of ±0.2° 2θ to account for this experimental error. As to PXRD patterns in their entirety, the term "as depicted" in a particular figure is meant to account for this experimental error, as well as for variations in peak position and intensity due to factors such as, for example, variations in sample preparation, instrumentation, and the skill of the operator of the instrument. A PXRD pattern "as depicted" in a particular figure means that one of ordinary skill in the art, understanding the experimental error involved in powder X-ray diffraction techniques, would determine that the PXRD pattern corresponds to the same crystalline structure as the PXRD pattern depicted in the figure.

The crystalline pemetrexed diacid Form A may be further characterized by data selected from a group consisting of: a weight loss of about 7.8% to about 8.8% at a temperature up to 160° C., as measured by thermal gravimetric analysis ("TGA"), and an X-ray powder diffraction pattern having peaks at about 5.6, 13.4, 16.8 and 25.1±0.2 degrees two-theta.

The crystalline pemetrexed diacid Form A is a hydrated form, and preferably a dihydrated form. The water content of the crystalline pemetrexed diacid is about 7.7% by weight, as measured by the Karl Fischer technique ("KF").

In addition, the crystalline pemetrexed diacid Form A has less than about 10% by weight, more preferably less than about 5% by weight, and most preferably less than about 1% by weight, of crystalline pemetrexed diacid characterized by an X-ray powder diffraction pattern having peaks at about 5.7, 12.2, 17.2 and 18.4 degrees two-theta±0.2 degrees two-theta. Typically, the content of crystalline pemetrexed diacid characterized by an X-ray powder diffraction pattern having peaks at about 5.7, 12.2, 17.2 and 18.4 degrees two-theta±0.2 degrees two-theta in the above form is determined by PXRD. The determination by PXRD can be done using the peak at 12.2 degrees two-theta±0.2 degrees two-theta.

The present invention also provides a process for preparing the crystalline pemetrexed diacid Form A. The process comprises crystallizing pemetrexed diacid from an aqueous solvent at a pH of about 4.5.

Preferably, the crystallization comprises: dissolving pemetrexed disodium in an aqueous solvent to obtain a solution, and adjusting the pH of the solution to about 4.5 to obtain a suspension comprising a precipitate of the crystalline pemetrexed diacid Form A.

Typically, the aqueous solvent is water or a mixture of water and a water-miscible organic solvent. Suitable water-miscible organic solvents include, but are not limited to ethanol, methanol, and acetonitrile. Preferably, the aqueous solvent is water.

Typically, the pH of the solution is adjusted by adding an acid. Preferably, the acid is provided in a form of a diluted aqueous solution. Preferably, the acid is HCl, HBr, $H_2SO_4$, trifluoroacetic acid, acetic acid, or p-toluenesulfonic acid, and more preferably HCl. Typically, the addition of the acid induces precipitation of the crystalline pemetrexed diacid.

The crystallization may further comprise heating the suspension and then cooling the suspension. These additional process steps are believed to aid in crystal growth. Preferably, the suspension is heated to a temperature of about 60° C. to about 70° C., and more preferably about 65° C. Preferably, the suspension is cooled to a temperature of about 30° C. to about 20° C., and more preferably to about 24° C. Preferably, the suspension is cooled for about 3 to about 7 hours, and more preferably about 5 hours.

Typically, the suspension is maintained to increase the yield of the precipitated crystalline pemetrexed diacid. Preferably, the suspension is maintained for about 8 to about 16 hours and more preferably for about 10 hours, preferably, with agitation.

The obtained crystalline pemetrexed diacid may be recovered from the suspension by any method known to a skilled artisan. Preferably, the crystalline pemetrexed diacid is recovered from the suspension by filtration. The recovered crystalline pemetrexed diacid may be washed with water adjusted to a pH of about 4.4 to about 4.6, more preferably about 4.5, and dried. Preferably, the drying is performed under vacuum, more preferably, at a pressure of about 18 mbar, at a temperature of about 35° C. to about 50° C., more preferably about 40° C. Preferably, the crystalline pemetrexed diacid is dried for about 10 to about 24 hours, and more preferably for about 17 hours.

The invention also encompasses crystalline pemetrexed diacid characterized by data selected from the group consisting of: a PXRD pattern having peaks at about 5.7, 12.2, 17.2 and 18.4 degrees two-theta±0.2 degrees two-theta; and a PXRD pattern as depicted in FIG. 2. This crystalline pemetrexed diacid can be designated as Form B.

The crystalline pemetrexed diacid Form B can be further characterized by data selected from a group consisting of: a PXRD pattern having peaks at about 11.5, 17.8, 22.8 and 26.7 degrees two-theta±0.2 degrees two-theta, and a weight loss of about 2.6% to about 3.8% at a temperature up to 220° C., as measured by TGA.

The crystalline pemetrexed diacid Form B is a hydrated form of pemetrexed diacid. The water content of the crystalline pemetrexed diacid is about 2.5% to about 3.9% by weight, as measured by KF.

In addition, the crystalline pemetrexed diacid Form B has less than about 15% by weight, preferably less than about 10% by weight, and more preferably less than about 5% by weight, of crystalline pemetrexed diacid characterized by an X-ray powder diffraction pattern having peaks at about 10.0, 10.3, 22.0 and 25.7 degrees two-theta±0.2 degrees two-theta. Typically, the content of crystalline pemetrexed diacid characterized by an X-ray powder diffraction pattern having peaks at about 10.0, 10.3, 22.0 and 25.7 degrees two-theta±0.2 degrees two-theta in the above form is determined by PXRD. The determination by PXRD can be done using any one of the peaks at 10.0 and 10.3 degrees two-theta±0.2 degrees two-theta.

The invention further encompasses a process for preparing the crystalline pemetrexed diacid Form B. The process comprises providing a suspension of pemetrexed diacid in an aqueous solvent having a pH of about 3, and adjusting the pH of the suspension to about 4.5.

Preferably, the process comprises: dissolving pemetrexed disodium in an aqueous solvent to form a solution, adjusting the pH of the solution to about 3 to obtain a suspension, and adjusting the pH of the suspension to about 4.5 to obtain a precipitate of the crystalline pemetrexed diacid Form B.

Typically, the pH of about 3 is obtained by adding an acid to the solution. Preferably, the acid is provided in the form of a diluted aqueous solution. Preferably, the acid is HCl1, HBr, $H_2SO_4$, trifluoroacetic acid, acetic acid, or p-toluenesulfonic acid, and more preferably HCl. Typically, the addition of the acid induces precipitation of the crystalline pemetrexed diacid.

The process may further comprise heating the suspension, and then cooling the suspension, prior to adjusting the pH to about 4.5. These additional process steps are believed to aid in crystal growth. Preferably, the suspension is heated to a temperature of about 60° C. to about 70° C., and more preferably about 65° C. Preferably, the suspension is cooled to a temperature of about 30° C. to about 20° C., and more preferably to about 24° C. Preferably, the suspension is cooled for about 3 to about 8 hours, and more preferably about 5 hours.

Typically, the suspension is maintained to increase the yield of the precipitated crystalline pemetrexed diacid. Preferably, the suspension is maintained for about 8 to about 16 hours, and more preferably about 11.5 hours, preferably, with agitation.

The pH is typically adjusted to about 4.5 by adding a base to the suspension. Preferably, the base is an alkali metal hydroxide, such as sodium hydroxide, lithium hydroxide, or potassium hydroxide, and more preferably sodium hydroxide. Preferably, the sodium hydroxide is provided in a form of an aqueous solution. Preferably, the aqueous solution is a diluted aqueous solution.

The above crystalline pemetrexed diacid may be recovered from the suspension by any method known to a skilled artisan. Preferably, the crystalline pemetrexed diacid is recovered from the suspension by filtration. The recovered crystalline pemetrexed diacid may be washed with water adjusted to a pH of about 4.4 to about 4.6, more preferably 4.5, and dried. Preferably, the drying is performed under vacuum, more preferably at a pressure of about 18 mbar, at a temperature of about 30° C. to about 80° C., more preferably about 40° C. Preferably, the crystalline pemetrexed diacid is dried for about 10 to about 25 hours, and more preferably for about 17 hours.

The invention also encompasses another process for preparing the crystalline pemetrexed diacid Form B. The process comprises slurrying in water crystalline pemetrexed diacid characterized by data selected from a group consisting of: a PXRD pattern having peaks at about 6.2, 10.7, 12.0 and 18.9 degrees two-theta±0.2 degrees two-theta, and a PXRD pattern as depicted in FIG. 4.

Preferably, the starting crystalline pemetrexed diacid is slurried in about 6 to 9 volumes of water, i.e., 6 to 9 milliliters of water per gram of crystalline pemetrexed diacid. More preferably, the starting crystalline pemetrexed diacid is slurried in about 7 to 8 volumes of water. Preferably, the starting crystalline pemetrexed is slurried at a temperature of about 50° C. Preferably, the slurrying is done for about 1 to about 3 hours.

Typically, the heated slurry is then cooled. Preferably, the heated slurry is cooled to a temperature of about 0° C. to about 24° C. Preferably, the cooling is conducted over a period of about 1 to 2 hours. After cooling, the slurry can be further maintained for about 1 to about 3 hours.

The obtained crystalline pemetrexed diacid may then be recovered from the slurry by any method known to one of ordinary skill in the art. Such methods include filtering the crystalline pemetrexed diacid from the slurry, followed by drying. Preferably, the drying is performed under vacuum with heating. Preferably, the drying is performed at a temperature of about 70° C. at a pressure of about 18 mbar, for about 18 hours. The crystalline pemetrexed diacid Form B thus prepared is illustrated by the PXRD pattern shown in FIG. 8. The PXRD pattern of FIG. 8 contains the characteristic peaks of pemetrexed diacid form B as described above, as well as additional peaks at 6.0 and 12.6 degrees two-theta±0.2 degrees two-theta The invention also encompasses crystalline pemetrexed diacid characterized by data selected from the group consisting of: a PXRD pattern as depicted in FIG. 3. This crystalline pemetrexed diacid can be designated as Form C.

The crystalline pemetrexed diacid Form C can be further characterized by data selected from a group consisting of: a PXRD pattern having peaks at about 9.2, 11.7, 12.8 and 19.6 degrees two-theta±0.2 degrees two-theta; and a two-step weight loss, where the first is of about 2.3% at a temperature up to 140° C., due to loss of water, and the second, is of about 2.9% at a temperature up to 200° C., due to loss of dimethylsulfoxide ("DMSO"), as measured by TGA.

The crystalline pemetrexed diacid Form C is a solvated form of pemetrexed diacid and preferably a DMSO solvate.

In addition, the crystalline pemetrexed diacid Form C has less than 15% by weight, more preferably less than 10% by weight, and most preferably, less than 5% by weight, of crystalline pemetrexed diacid characterized by an X-ray powder diffraction pattern with peaks at about 5.7, 12.2, 17.2 and 18.4 degrees two-theta±0.2 degrees two-theta. Typically, the content of crystalline pemetrexed diacid characterized by an X-ray powder diffraction pattern having peaks at about 5.7, 12.2, 17.2 and 18.4 degrees two-theta±0.2 degrees two-theta in the above form is determined by PXRD. The determination by PXRD can be done using the peak at 17.2 degrees two-theta±0.2 degrees two-theta.

The invention also encompasses a process for preparing the crystalline pemetrexed diacid Form C. The process comprises crystallizing pemetrexed diacid from a mixture comprising DMSO as a solvent and a mixture of water and at least one $C_{1-4}$ alcohol as an anti-solvent.

Typically, the crystallization is performed by combining the pemetrexed diacid and DMSO to obtain a solution, and admixing with the anti-solvent to precipitate the crystalline pemetrexed diacid Form C.

The starting pemetrexed diacid may be prepared according to any process known to a skilled artisan. For example, the pemetrexed diacid can be prepared according to the process described in *Org. Proc. Res. Dev.* 2005, pp. 738-742, which is incorporated herein by reference.

Typically, the solution of pemetrexed diacid in DMSO is provided by heating a combination of pemetrexed diacid and DMSO. Preferably, the combination is heated to about 25° C. to about 75° C., and more preferably about 65° C.

Preferably, the pemetrexed diacid is combined with the DMSO in a ratio of about 1:1 to about 1:3 g/mL, respectively.

Typically, the anti-solvent is admixed with the solution. Preferably, the anti-solvent and the solution are admixed at a temperature of about 30° C. to about 65° C., and more preferably at about 40° C. to about 50° C. The anti-solvent is, preferably, added to the solution. Preferably, the anti-solvent is added to the solution drop-wise. Preferably, the anti-solvent is added drop-wise to the solution over a period of about 1 hour to about 5 hours, and more preferably about 1 hour to about 2.5 hours.

Suitable $C_{1-4}$ alcohols include, but are not limited to methanol, ethanol, isopropanol, propanol, isobutanol, and butanol. Preferably, the mixture of water and a $C_{1-4}$ alcohol, is that of methanol and water. Preferably, the ratio of the $C_{1-4}$ alcohol and water in the anti-solvent mixture is of about 1:3 to about 3:1 vol./vol., respectively. Typically, admixing the anti-solvent with the solution forms a suspension comprising a precipitate of the said crystalline pemetrexed diacid.

Usually, the suspension is maintained to increase the yield of the precipitated crystalline pemetrexed diacid. Preferably, the suspension is maintained at a temperature of about 30° C. to about 65° C. Preferably, the suspension is maintained for about 20 minutes to about three hours, and more preferably for about 30 minutes to about 1.5 hours. Preferably, the suspension is maintained while being stirred.

The yield of the crystalline pemetrexed diacid Form C may also be increased by cooling the suspension to induce further precipitation of the crystalline pemetrexed diacid. Preferably, the suspension is cooled to a temperature of about 30° C. to about 0° C., and more preferably to about 25° C. to about 10° C. Preferably, the cooling is performed over a period of about 1 to about 6 hours, and more preferably about 2 to about 4 hours. Preferably, the cooled suspension is maintained for about 0.5 to about 6 hours, and more preferably for about 2 to about 4 hours, prior to recovering the crystalline pemetrexed diacid.

The obtained crystalline pemetrexed diacid may be recovered by any method known to a skilled artisan. Preferably, the crystalline pemetrexed diacid is recovered from the suspension by filtration. The recovered crystalline pemetrexed diacid may be washed and dried. The recovered pemetrexed diacid may be washed with water or a mixture of water and methanol. The recovered pemetrexed diacid may be dried under vacuum with heating. Preferably, the recovered pemetrexed diacid is dried at a temperature of about 35° C. to about 50° C., at a pressure of about 18 mbar, for about 24 to about 72 hours.

The recovered crystalline pemetrexed diacid may optionally be further purified by slurrying in the anti-solvent. Preferably, the recovered crystalline pemetrexed diacid is washed with the anti-solvent prior to slurrying it. The preferred anti-solvent for washing is water or a mixture of water and methanol. Optionally, the washed crystalline pemetrexed diacid may be dried prior to slurrying it. The drying may be done at a temperature of about 35° C. to about 45° C., and more preferably about 40° C., under vacuum, preferably at a pressure of about 18 mbar.

Preferably, the slurrying is performed at a temperature of about 5° C. to about 65° C., and more preferably at about 35° C. to about 50° C. Preferably, the slurrying is performed for about 0.5 hour to about 4 hours, and more preferably for about 1 hour to about 2 hours. Preferably, the anti-solvent used for slurrying is selected from the group consisting of water, ethanol, methanol and mixtures thereof.

Typically, the slurry is cooled prior to recovering the purified crystalline pemetrexed diacid Form C. Preferably, the slurry is cooled to a temperature of about 30° C. to about 5° C., and more preferably about 25° C. to about 10° C.

The purified crystalline pemetrexed diacid may be recovered from the slurry by any method known to a skilled artisan. Preferably, the purified crystalline pemetrexed diacid is recovered from the slurry by filtration. The recovered crystalline pemetrexed diacid may then be dried.

The invention also encompasses crystalline pemetrexed diacid characterized by data selected from the group consisting of: a PXRD pattern having peaks at about 6.2, 10.7, 12.0 and 18.9 degrees two-theta±0.2 degrees two-theta; and a PXRD pattern as depicted in FIG. 4. This crystalline pemetrexed diacid can be designated as Form D.

The crystalline pemetrexed diacid Form D can be further characterized by data selected from a group consisting of: a PXRD pattern having peaks at about 13.9 and 17.4 degrees two-theta±0.2 degrees two-theta; and a two-step weight loss; where the first is of about 1.5% to about 3.6% at a temperature up to 140° C., due to loss of water, and the second, is of about 8.6% to about 12.3% at a temperature up to 190° C., due to loss of dimethylformamide ("DMF"), as measured by TGA.

The crystalline pemetrexed diacid Form D is a solvated form of pemetrexed diacid, and preferably a DMF solvate.

The crystalline pemetrexed diacid Form D has less than about 10% by weight, more preferably less than about 5% by weight, and most preferably less than about 1% by weight, of crystalline pemetrexed diacid characterized by an X-ray powder diffraction pattern having peaks at about 5.7, 12.2, 17.2 and 18.4 degrees two-theta±0.2 degrees two-theta. Typically, the content of crystalline pemetrexed diacid characterized by an X-ray powder diffraction pattern having peaks at about 5.7, 12.2, 17.2 and 18.4 degrees two-theta±0.2 degrees two-theta in the above form is determined by PXRD. The determination by PXRD can be using any one of the peaks at 5.7, 17.2 and 18.4 degrees two-theta±0.2 degrees two-theta.

The invention also encompasses a process for preparing the above crystalline pemetrexed diacid. The process comprises crystallizing pemetrexed diacid from a mixture comprising DMF as a solvent and a mixture of water and methanol as an anti-solvent.

Typically, the crystallization is performed by combining the pemetrexed diacid and the DMF to obtain a solution, and admixing with the anti-solvent to precipitate the crystalline pemetrexed diacid Form D.

Typically, the solution of pemetrexed diacid in DMF is provided by heating a combination of pemetrexed diacid and DMF. Preferably, the combination is heated to about 30° C. to about 65° C., and more preferably about 50° C.

Typically, the anti-solvent is admixed with the solution at a temperature of about 30° C. to about 65° C., and more preferably at about 50° C. The anti-solvent is, preferably, added to the solution. Preferably, the anti-solvent is added to the solution drop-wise. Preferably, the anti-solvent is added drop-wise to the solution over a period of about 80 minutes.

Preferably, the ratio of the methanol and water in the anti-solvent mixture is of about 1:3 to about 3:1 vol./vol, respectively. Typically, admixing the anti-solvent with the solution forms a suspension comprising a precipitate of the said crystalline pemetrexed diacid.

Usually, the suspension is maintained to increase the yield of the precipitated crystalline pemetrexed diacid. Preferably, the suspension is maintained at a temperature of about 30° C. to about 55° C. Preferably, the suspension is maintained for about 2 to about 6 25 hours, and more preferably for about 3 hours. Preferably, the suspension is maintained while being stirred.

The yield of the crystalline pemetrexed diacid may also be increased by cooling the suspension to induce further precipitation of the crystalline pemetrexed diacid. Preferably, the suspension is cooled to a temperature of about 20° C. to about 30° C., and more preferably about 28° C. Preferably, the cooling is performed over a period of about 1 to about 3 hours, and more preferably about 2 hours. Preferably, the cooled suspension is maintained for about 0.5 to about 6 hours, and more preferably for about 2 to about 4 hours, prior to recovering the crystalline pemetrexed diacid.

The obtained crystalline pemetrexed diacid may be recovered by any method known to a skilled artisan. Preferably, the crystalline pemetrexed diacid is recovered from the suspension by filtration. The recovered crystalline pemetrexed diacid may be washed and dried. The recovered crystalline pemetrexed diacid may be washed with water or—a mixture of water and methanol. The recovered crystalline pemetrexed diacid may be dried under vacuum with heating. Preferably, the recovered pemetrexed diacid is dried at a temperature of about 30° C. to about 50° C., and preferably about 40° C., under vacuum, preferably at a pressure of about 18 mbar.

The invention also encompasses crystalline pemetrexed diacid characterized by data selected from the group consisting of: a PXRD pattern having peaks at about 9.0, 16.2, 18.1 and 26.9 degrees two-theta±0.2 degrees two-theta; and a PXRD pattern as depicted in FIG. 5. This crystalline pemetrexed diacid can be designated as Form E.

The crystalline pemetrexed diacid Form E can be further characterized by data selected from the group consisting of: a PXRD pattern having peaks at about 5.8, 6.9, 12.0, 18.8, and 19.6 degrees two-theta±0.2 degrees two-theta; and a two-step weight loss; where the first is of about 2.5% at a temperature up to 100° C., due to loss of water, and the second, is of about 11.7% at a temperature up to 200° C., due to loss of DMF, as measured by TGA.

The crystalline pemetrexed diacid Form E is a solvated form of pemetrexed diacid, and preferably a DMF solvate.

In addition, the crystalline pemetrexed diacid Form E has less than about 15% by weight, more preferably less than about 10% by weight, and most preferably less than about 5% by weight, of crystalline pemetrexed diacid characterized by an X-ray powder diffraction pattern having peaks at about 5.7, 12.2, 17.2 and 18.4 degrees two-theta±0.2 degrees two-theta. Typically, the content of crystalline pemetrexed diacid characterized by an X-ray powder diffraction pattern having peaks at about 5.7, 12.2, 17.2 and 18.4 degrees two-theta±0.2 degrees two theta in the above form is determined by PXRD. The determination by PXRD can be done using the peak at 17.2 degrees two-theta±0.2 degrees two-theta.

The invention further encompasses a process. for preparing the crystalline pemetrexed diacid Form E. The process comprises crystallizing pemetrexed diacid from a mixture comprising DMF as a solvent, and ethanol as an anti-solvent.

Typically, the crystallization is performed by combining the pemetrexed diacid and the DMF to obtain a solution, and admixing with ethanol to precipitate the crystalline pemetrexed diacid Form E.

Typically, the solution of pemetrexed diacid in DMF is provided by heating a combination of pemetrexed diacid and DMF. Preferably, the combination is heated to about 40° C. to about 60° C., and more preferably about 50° C.

Typically, the anti-solvent is admixed with the solution at a temperature of about 40° C. to about 60° C., and more preferably at about 50° C. The anti-solvent is, preferably, added to the solution. Preferably, the anti-solvent is added to the solution drop-wise. Preferably, the anti-solvent is added drop-wise to the solution over a period of about 0.5 hour to 1.5 hours, and more preferably about 45 minutes.

Preferably, the ethanol is absolute ethanol. Typically, admixing the anti-solvent with the solution forms a suspension comprising the crystalline pemetrexed diacid Form E.

The yield of the crystalline pemetrexed diacid Form E may be increased by cooling the suspension to further induce precipitation of the crystalline pemetrexed diacid. Preferably, the suspension is cooled to a temperature of about 30° C. to about 0° C., and more preferably to about room temperature.

The yield of the crystalline pemetrexed diacid may also be increased by combining the cooled suspension with an additional amount of ethanol to induce further precipitation of the crystalline pemetrexed diacid. The total amount of ethanol can be, optionally, added at one portion. After the addition of the second amount of the ethanol, the ratio between the DMF solvent and ethanol is preferably, of about 1:1 to about 1:10, vol./vol., respectively, more preferably, of about 1:5.5 vol./vol., respectively. The new suspension, obtained after the addition of the second amount of ethanol, is then preferably maintained again, prior to recovering the product. Preferably, the new suspension is maintained for about 2 to about 24 hours, more preferably, of about 18 hours.

The obtained crystalline pemetrexed diacid may be recovered by any method known to a skilled artisan. Preferably, the crystalline pemetrexed diacid is recovered from the suspension by filtration. The recovered crystalline pemetrexed diacid may be washed and dried. The recovered pemetrexed diacid may be washed with ethanol. The recovered pemetrexed diacid may be dried under vacuum with heating. Preferably, the recovered pemetrexed diacid is dried at a temperature of about 35° C. to about 50° C., at a pressure of about 18 mbar, for about 24 to about 72 hours.

The invention also encompasses crystalline pemetrexed diacid characterized by data selected from the group consisting of: a PXRD pattern having peaks at about 7.7, 9.2, 16.7 and 27.4 degrees two-theta±0.2 degrees two-theta; and a PXRD pattern as depicted in FIG. 6. This crystalline pemetrexed diacid can be designated as Form F.

The crystalline pemetrexed diacid Form F can be further characterized by data selected from the group consisting of: a PXRD pattern having peaks at about 14.2, 15.4, 18.5, and 20.5 degrees two-theta±0.2 degrees two-theta; and a weight loss of about 0.2% to about 0.3% at a temperature up to 190° C., as measured by TGA.

The crystalline pemetrexed diacid Form F is an anhydrous form of pemetrexed diacid. As used herein, unless otherwise defined, the term "anhydrous" when referring to pemetrexed diacid means a substance having a weight loss not more than 1% by TGA.

The crystalline pemetrexed diacid Form F has less than about 10% by weight, more preferably less than about 5% by weight, and most preferably less than about 1% by weight, of crystalline pemetrexed diacid characterized by an X-ray powder diffraction pattern having peaks at about 5.7, 12.2, 17.2 and 18.4 degrees two-theta±0.2 degrees two-theta.

Typically, the content of crystalline pemetrexed diacid characterized by an X-ray powder diffraction pattern having peaks at about 5.7, 12.2, 17.2 and 18.4 degrees two-theta±0.2 degrees two-theta in the above form is determined by PXRD. The determination by PXRD can be done using the peak at 12.2 degrees two-theta±0.2 degrees two-theta.

The invention also encompasses a process for preparing the crystalline pemetrexed diacid Form F. The process comprises admixing N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic acid salt of the following formula

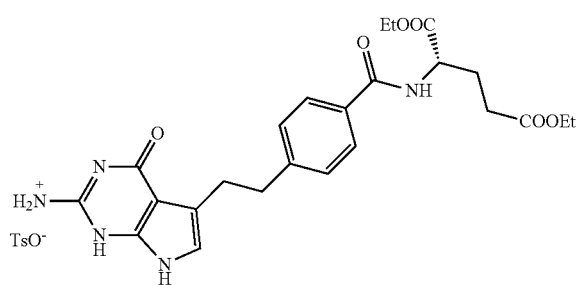 [SMILES: "TsO-" ; CCOC(=O)CC[C@H](NC(=O)c1ccc(CCc2c[nH]c3[nH]c(N)nc(=O)c23)cc1)C(=O)OCC]

and at least one base to obtain a solution, and adding the solution to an acid to obtain a suspension comprising the said crystalline pemetrexed diacid.

The starting N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic acid salt can be obtained, for example, according to the process disclosed in U.S. Pat. No. 6,262,262, hereby incorporated by reference.

Typically, the N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic acid salt is first combined with water and then with the base to obtain the solution. The base can be an organic or inorganic base. Preferably, the organic base is triethylamine or diisopropylamine Preferably, the inorganic base is sodium hydroxide, potassium hydroxide, sodium carbonate or lithium hydroxide, and more preferably sodium hydroxide. The inorganic base can be used in its solid form or in a form of an aqueous solution.

Typically, combining the base and the N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic salt provides a salt of pemetrexed diacid, which is soluble in water.

The solution of the salt has a basic pH, preferably, of about 11 to about 14. Combining the base and the N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic acid salt is typically exothermic, and, thus, is performed with cooling. Preferably, the cooling is to a temperature of about 20° C. to about 0° C., more preferably, to about 2° C.

The acid may be a mineral acid or an organic acid. Preferably, the mineral acid is $H_2SO_4$, HCl, or HBr. Preferably, the organic acid is methanesulfonic acid or toluenesulfonic acid. More preferably, the acid is HCl. Typically, the acid is provided in the form of an aqueous solution. The aqueous solution may be generated by combining a concentrated acid with water.

Adding the solution to the acid is typically exothermic. To reduce the exotherm, the solution and/or the acid may be cooled during the addition. The solution may also be added drop-wise to the acid to reduce the exotherm. The cooling is, preferably, to a temperature of about 20° C. to about 0° C., more preferably, to about 2° C. Preferably, the drop-wise addition is done over a period of about 15 to about 45 minutes, more preferably, of about 20 minutes.

Typically, the solution is added to the acid while stirring to ensure the occurrence of the reaction. Typically, the acid neutralizes the salt, providing a suspension comprising free pemetrexed diacid.

The suspension is then typically heated. Preferably, the suspension is heated to a temperature of about 60° C. to about 80° C., and more preferably about 70° C. Preferably, the heating is done for about I hour to about 4 hours, and more preferably for about 2 hours.

Typically, the suspension is cooled prior to recovering the crystalline pemetrexed diacid Form F. The suspension is preferably cooled to a temperature of about 30° C. to about 10° C., and more preferably to about 20° C. Preferably, the cooling is done for a period of about 1.5 hours to 3 hours, and more preferably for about 2 hours. Typically, the cooled slurry is maintained while stirring for a period of about 3 to about 6 hours, more preferably, for about 4 hours.

The obtained crystalline pemetrexed diacid may be recovered by any method known to a skilled artisan. Preferably, the crystalline pemetrexed diacid is recovered from the suspension by filtration. The recovered crystalline pemetrexed diacid may be washed and dried. The recovered pemetrexed diacid may be washed with water. The recovered pemetrexed diacid may be dried under vacuum with heating. Preferably, the recovered pemetrexed diacid is dried at a temperature of about 70° C., at a pressure of about 18 mbar, for about 10 to about 16 hours.

The invention also encompasses crystalline pemetrexed diacid characterized by data selected from the group consisting of: a PXRD pattern having peaks at about 6.8, 11.9, 15.5 and 17.9 degrees two-theta±0.2 degrees two-theta; and a PXRD pattern as depicted in FIG. 7. This crystalline pemetrexed diacid can be designated as Form G.

The crystalline pemetrexed diacid Form G may be further characterized by data selected from a group consisting of: a PXRD pattern having peaks at about 8.9, 20.5, and 24.1 degrees two-theta±0.2 degrees two-theta; and a weight loss of about 0.6% to about 0.9% at a temperature up to 120° C., as measured by TGA.

The crystalline pemetrexed diacid Form G is an anhydrous form of pemetrexed diacid.

In addition, the crystalline pemetrexed diacid Form G has less than about 15% by weight, more preferably less than about 10% by weight, and most preferably less than about 5% by weight, of crystalline pemetrexed diacid characterized by an X-ray powder diffraction pattern having peaks at about 5.7, 12.2, 17.2 and 18.4 degrees two-theta±0.2 degrees two-theta. Typically, the content of crystalline pemetrexed diacid characterized by an X-ray powder diffraction pattern having peaks at about 5.7, 12.2, 17.2 and 18.4 degrees two-theta±0.2 degrees two-theta in the above form is determined by PXRD. The determination by PXRD can be done using the peak at 12.2 degrees two-theta±0.2 degrees two-theta.

The invention also encompasses a process for preparing the crystalline pemetrexed diacid Form G. The process comprises heating a crystalline form of pemetrexed diacid selected from the group consisting of: crystalline pemetrexed diacid characterized by an X-ray powder diffraction pattern having peaks at about 5.7. 12.2, 17.2 and 18.4 degrees two-theta±0.2 degrees two-theta; crystalline pemetrexed diacid characterized by an X-ray powder diffraction pattern having peaks at about 5.8, 12.4, 18.6 and 24.6 degrees two-theta±0.2 degrees two-theta; crystalline pemetrexed diacid characterized by an X-ray powder diffraction pattern having peaks at about 9.0, 16.2, 18.1 and 26.9 degrees two-theta±0.2 degrees~a-theta; and mixtures thereof.

Typically, the crystalline form of pemetrexed diacid is heated to a temperature of about 160° C. to about 200° C., preferably about 180° C. to about 200° C., to effect conversion to the said crystalline pemetrexed diacid.

The crystalline form of pemetrexed diacid can be heated in one step or gradually. Gradual heating preferably includes two stages of heating. Preferably, the first stage of heating is to a temperature of about 100° C. to about 160° C. Preferably, the first stage of heating is for about 30 minutes to about 1 hour. Preferably, the second stage of heating is to a temperature of about 180° C. to about 200° C. Preferably, the second stage of heating is for about 20 to about 40 minutes, more preferably, for about 0.5 hour.

The invention also encompasses an additional process for preparing the crystalline pemetrexed diacid Form G. The process comprises drying crystalline pemetrexed diacid characterized by an X-ray powder diffraction pattern having peaks at about 10.0, 10.3, 22.0 and 25.7 degrees two-theta±0.2 degrees two-theta at a temperature of about 200° C. for about 30 minutes.

The invention also encompasses another process for preparing the crystalline pemetrexed diacid Form G. The process comprises drying crystalline pemetrexed diacid characterized by an X-ray powder diffraction pattern having peaks at about 6.2, 10.7, 12.0 and 18.9 degrees two-theta±0.2 degrees two-theta at a temperature of about 200° C. for about 30 minutes.

The invention also encompasses a process for preparing a pharmaceutically acceptable salt of pemetrexed diacid comprising preparing any of the above crystalline pemetrexed diacid by the processes of the invention, and converting them to the pharmaceutically acceptable salt of pemetrexed diacid. Preferably, the pharmaceutically acceptable salt is pemetrexed disodium. The conversion can be done, for example, according to the process disclosed in U.S. publication No. 2003/0216416, hereby incorporated by reference The invention also encompasses a process for preparing a lyophilized form of a pharmaceutically acceptable salt of pemetrexed comprising preparing any of the above crystalline forms of pemetrexed diacid by the processes of the invention, and converting them to the lyophilized pharmaceutically acceptable salt of pemetrexed. Preferably, the pharmaceutically acceptable salt is pemetrexed disodium. This conversion may be done, for example, according to the process disclosed in co-pending U.S. application Ser. No. 11/893,212 filed Aug. 14, 2007, entitled "Processes for the Preparation of Lyophilized Pharmaceutically Acceptable Salts of Pemetrexed Diacid," as 5 well as U.S. application Serial Nos. 60/847,291, filed Sep. 25, 2006; 60/855,139, filed Oct. 30, 2006; 60/880,179, filed Jan. 11, 2007; and 60/958,326, filed Jul. 2, 2007, all of which are incorporated herein by reference.

Any of the above crystalline forms of pemetrexed diacid can be converted into a lyophilized pharmaceutically acceptable salt of pemetrexed diacid by a process comprising: combining the crystalline form of pemetrexed diacid, an agent capable of forming a pharmaceutically acceptable salt of pemetrexed, and a solvent comprising water or a mixture of water and a solvent suitable for lyophilization to obtain a mixture comprising a pharmaceutically acceptable salt of pemetrexed; and removing the solvent by lyophilization to obtain a lyophilized pharmaceutically acceptable salt of pemetrexed; wherein the pharmaceutically acceptable salt of pemetrexed is not isolated prior to the lyophilization process; and the pharmaceutically acceptable salt of pemetrexed is a di-base-addition salt of pemetrexed.

As used herein, unless otherwise, defined, an "agent capable of forming a pharmaceutically acceptable salt of pemetrexed" refers to an agent that is capable of forming a base-addition salt of pemetrexed. Base-addition salts include, but are not limited to, alkali or alkaline earth metal salts, such as sodium, potassium, lithium, and calcium salts.

Preferably, the agent capable of forming a pharmaceutically acceptable salt of pemetrexed is an alkali (preferably sodium) or alkaline earth metal hydroxide, carbonate, phosphate, or sulfate. More preferably, the agent capable of forming a pharmaceutically acceptable salt of pemetrexed is an alkali or alkaline earth metal hydroxide, and most preferably sodium hydroxide.

In a preferred embodiment, initially, the crystalline form of pemetrexed diacid is combined with the solvent to obtain a first mixture. Preferably, the solvent is water. When a mixture of water and a solvent suitable for lyophilization is used, the solvent suitable for lyophilization may include, but is not limited to, tert-butanol, dimethylsulfoxide, or 1,4-dioxane. Preferably, the solvent suitable for lyophilization is tert-butanol.

The first mixture is then admixed with an alkali or alkaline earth metal hydroxide to obtain the mixture comprising the pharmaceutically acceptable salt of pemetrexed.

Preferably, the alkali or alkaline earth metal hydroxide is NaOH, KOH, LiOH, or $C_a(OH)_2$, and more preferably, NaOH.

Preferably, the alkali or alkaline earth metal hydroxide is added to the first mixture. Preferably, the mixture is a solution.

Typically, to obtain the pharmaceutically acceptable salt of pemetrexed from the crystalline form of pemetrexed diacid, at least about 1 mole equivalent of alkali or alkaline earth metal hydroxide per mole equivalent of the starting crystalline form of pemetrexed diacid is used. Preferably, the alkali hydroxide is used in an amount of about 1 to about 3 mole equivalents per mole equivalent of the starting crystalline form of pemetrexed diacid or salt thereof.

The alkali hydroxide may be in solution or solid form. Preferably, the alkali or alkaline earth metal hydroxide is in the form of an aqueous solution. Preferably, the aqueous solution of the alkali or alkaline earth metal hydroxide is a standard solution. As used herein, unless otherwise defined, the term "standard solution" refers to a solution having a known concentration, where the concentration is determined by various methods known to a skilled artisan, such as titration with acids. Preferably, the standard solution of the alkali or alkaline earth metal hydroxide has a concentration of about 0.5 M to about 4 M, more preferably, of about 2 M.

Preferably, admixing the first mixture and the alkali or alkaline earth metal hydroxide solution is performed at a temperature of about 1° C. to about 100° C., more preferably at about 10° C. to about 60° C., and most preferably at about 15° C. to about 40° C.

As a skilled artisan will appreciate, complete dissolution or a stable pH value of about 7.0 to 7.5, or, more preferably, 7.1 to 7.2, is an indication that the reaction has completed.

The process for preparing lyophilized pharmaceutically acceptable salt of pemetrexed may further comprise a process of adjusting the pH to obtain a pH of about 7.0 to about 10.0 preferably, of about 7.0 to about 9.0, more preferably, of about 7.0 to about 8.0, and most preferably, of about 7.0 to about 7.5, prior to lyophilizing the solution comprising the pharmaceutically acceptable salt of pemetrexed. The pH can be adjusted by admixing the solution comprising the pharmaceutically acceptable salt of pemetrexed with alkali hydroxide or with any one of the starting materials, depending on the pH of the solution. Typically, the pH measurement is done by using a pH-meter.

Optionally, a dispersing agent may be added to the mixture before removing the solvent. Preferably, the dispersing agent is a sugar such as lactose, fructose or mannitol. Preferably, the sugar is mannitol. Preferably, the dispersing agent is present in an equimolar amount in weight relative to the amount of the pharmaceutically acceptable salt of pemetrexed.

Having described the invention with reference to certain preferred embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Experimental Methodology (physical):
Powder X-ray Diffraction:

Powder-ray diffraction was performed on a ARL X-ray powder diffractometer model X'TRA-030, with a Peltier detector. Round standard aluminum sample holders with round zero background quartz plates were used. The scanning parameters were as follows: 15 Range: 2-40 deg. 2θ, continuous Scan, Rate: 3 deg./min. The accuracy of peak positions is defined as +/−0.2 degrees due to experimental differences such as instrumentation and sample preparation.
Thermal Gravimetric Analysis:
TGA/SDTA 851$^e$, Mettler Toledo, Sample weight 7-15 mg. Heating rate: 10° C./min., In $N_2$ stream: flow rate=50 ml/min
Scan range: 30-250° C. or 30-280° C.

Example 1

Preparation of Crystalline Pemetrexed Diacid Characterized by an X-Ray Powder Diffraction Pattern Having Peaks at about 10.0, 10.3, 22.0 and 25.7 Degrees Two-Theta±0.2 Degrees Two-Theta A flask was charged with N-[4-[2-(2-amino-4,7-dihydro-4-oxo-1H-pyrrolo[2,3-d]pyrimidin-5-yl)ethyl]benzoyl]-L-glutamic acid disodium salt (23.89 g) and water (478 ml) and stirred for 20 minutes at 24° C., to achieve complete dissolution. The pH of the resulting solution was adjusted to about 4.5 by the addition of diluted hydrochloric acid, after which abundant solid formation was observed. The resulting suspension was then heated to 65° C. for 25 minutes, was slowly cooled to 24° C. over a period of 5 hours, and was then stirred at 24° C. for 10 hours. The solid was filtered from the suspension and washed two times (2×50 ml) with water adjusted to pH 4.5 with hydrochloric acid. The wet solid was dried at 40° C. under vacuum (18 mbar) for 16.5 hours to afford the title compound as a white, fine solid (7.20 g). The X-ray powder diffraction pattern of the dry material was measured and is illustrated in FIG. 1.

Example 2

Preparation of Crystalline Pemetrexed Diacid Characterized by an X-Ray Powder Diffraction Pattern Having Peaks at about 5.7, 12.2, 17.2 and 18.4 Degrees Two-Theta±0.2 Degrees Two-Theta A flask was charged with N-[4-[2-(2-amino-4,7-dihydro-4-oxo-1H-pyrrolo[2,3-d]pyrimidin-5-yl)ethyl]benzoyl]-L-glutamic acid disodium salt (12.77 g) and water (240 ml) and stirred at 24° C. to achieve complete dissolution. The pH of the resulting solution was adjusted to about 3.0 by the addition of hydrochloric acid, after which abundant solid formation was observed. The resulting suspension was then heated to 65° C. for 35 minutes, was slowly cooled to 24° C. over a period of 5 hours, and was then stirred at 24° C. for 11.5 hours. The pH of the suspension was then adjusted to about 4.5 by the addition of 2.0M sodium hydroxide, and the suspension was stirred at 24° C. for 50 minutes. The solid was filtered from the suspension and washed two times (2×50 ml) with water adjusted to pH 4.5 with hydrochloric acid. The wet solid was dried at 40° C. under vacuum (18 mbar) for 15.5 hours to afford the title compound as a white-grey solid (8.32 g). The X-ray powder diffraction pattern of the dry material was measured and is illustrated in FIG. 2.

Example 3

Preparation of Crystalline Pemetrexed Diacid Characterized by an X-Ray Powder Diffraction Pattern Having Peaks at about 5.8, 12.4, 18.6 and 24.6 Degrees Two-Theta±0.2 Degrees Two-Theta A flask was charged with N-[4-[2-(2-amino-4,7-dihydro-4-oxo-1H-pyrrolo[2,3-d]pyrimidin-5-yl)ethyl]benzoyl]-L-glutamic acid (98.22% HPLC purity) (10.0 g) and dimethylsulfoxide (25 ml), heated to 65° C. and stirred until complete dissolution. Methanol (37.5 ml) and water (37.5 mL) was then added drop-wise to the solution over a period of about 2.5 hours. The resulting suspension was stirred for 1 hour at 65° C. and then was cooled to 22° C. over a period of about 2.5 hours. The suspension was filtered and the isolated solid was washed with a mixture of water (50 ml) and methanol (50 mL). The solid was then dried at 40° C. under vacuum (18 mbar) for about 16 hours, to afford pemetexed diacid (7.62 g) in 99.16% purity (HPLC).

A 2 g sample of the dry pemetrexed acid was slurried in 15 mL of water to form a suspension. The suspension was then heated at 50° C. for 1 h and then slowly cooled to ambient temperature and filtered. The resulting solid was dried in the oven at 80° C. under vacuum (18 mbar) for about 16 hours to afford the title compound in 99.46% purity (HPLC). The X-ray powder diffraction pattern of the dry material was measured and is illustrated in FIG. 3.

Example 4

Preparation of Pemetrexed Diacid Characterized by an X-Ray Powder Diffraction Pattern Having Peaks at about 6.2, 10.7, 12.0 and 18.9 Degrees Two-Theta±0.2 Degrees Two-Theta A flask was charged with N-[4-[2-(2-amino-4,7-dihydro-4-oxo-1H-pyrrolo[2,3-d]pyrimidin-5-yl)ethyl]benzoyl]-L-glutamic acid (99.00% HPLC purity) (3.64 g) and dimethylformamide (7.3 ml), heated to 50° C. and stirred until complete dissolution. A mixture of water (10.9) and methanol (18.2 ml) was then added drop-wise to the solution over a period of about 80 minutes. The obtained suspension was stirred for 30 minutes at 50° C. and then cooled to 30° C. over a period of about 2 hours. The suspension was filtered and the solid was washed with water (20 ml).

The wet solid was dried at 40° C. under vacuum (18 mbar) for about 72 hours to afford the title compound as a light-blue solid (3.02 g) in 99.32% purity (HPLC). The X-ray powder diffraction pattern of the dry material was measured and is illustrated in FIG. 4.

Example 5

Preparation of Pemetrexed Diacid Characterized by an X-Ray Powder Diffraction Pattern Having Peaks at about 9.0, 16.2, 18.1, and 26.9 Degrees Two-Theta±0.2 Degrees Two-Theta Pemetrexed Diacid (3.0 g) was dissolved in DMF (6.0 ml), the solution was heated at 50° C. for 45 minutes, absolute EtOH (18.0 ml) was added drop-wise over 15 minutes and the slurry was heated for 30 minutes more. The mixture was cooled to room temperature and other absolute EtOH (15.0 ml) was added to the suspension. The suspension was kept under stirring for 18 h, was filtered and washed with absolute EtOH (3×3.0 ml). The wet cake was dried at 40° C. under vacuum for 72 h, resulting 2.88 g (96.0%) of the pemetrexed diacid. The PXRD pattern of the dried pemetrexed diacid was measured and illustrated in FIG. 5.

Example 6

Preparation of Pemetrexed Diacid Characterized by an X-Ray Powder Diffraction Pattern Having Peaks at about 7.7, 9.2, 16.7, and 27.4 Degrees Two-Theta±0.2 Degrees Two-Theta 5 g of N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic Acid Salt was suspended at 2° C. in 50 mL water. 50 mL of aqueous sodium hydroxide (2M), previously cooled to 2° C., were added and the mixture was stirred for 1.5 hours at 2° C. Complete dissolution was observed. The solution was then added drop-wise, at 2° C., over 20 minutes, to a solution of 3.0 mL aqueous hydrochloric acid (37%) in 30 mL of water and the pH was corrected from 3.9 to 4.1 with aqueous sodium hydroxide 0.1N. The resulting suspension was stirred at 2° C. for 30 min. and heated at 70° C. for two hours. After cooling to 24° C. in 2 hours, the suspension was filtered and the solid was dried in the oven at 70° C. under vacuum (18 mbar) to yield the titled compound (75.17%). The PXRD pattern of the dried pemetrexed diacid was measured and illustrated in FIG. 6.

Example 7

Preparation of Pemetrexed Diacid Characterized by an X-Ray Powder Diffraction Pattern Having Peaks at about 6.8. 11.9. 15.5 and 17.9 Degrees Two-Theta±0.2 Degrees Two-Theta 250 mg sample of crystalline pemetrexed characterized by a PXRD pattern having peaks at about 5.7, 12.2, 17.2 and 18.4 degrees two-theta±0.2 degrees two-theta was kept in an oven at 160° C. for 1 hour and after it was kept at 200° C. for 30 minutes. The PXRD pattern of the dried pemetrexed diacid was measured and illustrated in FIG. 7.

Example 8

Preparation of Pemetrexed Diacid Characterized by an X-Ray Powder Diffraction Pattern with Peaks at about 6.8. 11.9. 15.5 and 17.9 Degrees Two-Theta±0.2 Degrees Two-Theta A 200 mg sample of the product of example 3 was kept in an oven at 100° C. for 30 minutes and after it was kept at 180° C. for 30 minutes. The X-ray powder diffraction pattern of the heat-treated material was measured.

Example 9

Preparation of Pemetrexed Diacid Characterized by an X-Ray Powder Diffraction Pattern with Peaks at about 6.8, 11.9, 15.5 and 17.9 Degrees Two-Theta±0.2 Degrees Two-Theta A 200 mg sample of the product of example 5 was kept in an oven at 100° C. for 30 minutes and after it was kept at 180° C. for 30 minutes. The X-ray powder diffraction pattern of the heat-treated material was measured.

Example 10

Preparation of Pemetrexed Diacid Characterized by an X-Ray Powder Diffraction Pattern Having Peaks at about 6.8. 11.9. 15.5 and 17.9 Degrees Two-Theta±0.2 Degrees Two-Theta A sample of crystalline pemetrexed diacid characterized by a PXRD pattern having peaks at about 10.0, 10.3, 22.0 and 25.7 degrees two-theta±0.2 degrees two-theta (about 150 mg) was kept in an oven at 200° C. for 30 minutes. The X-ray powder diffraction pattern of the dried crystalline pemetrexed diacid was measured.

Example 11

Preparation of Pemetrexed Diacid Characterized by an X-Ray Powder Diffraction Pattern Having Peaks at about 6.8, 11.9, 15.5 and 17.9 Degrees Two-Theta±0.2 Degrees Two-Theta A sample of crystalline pemetrexed diacid characterized by a PXRD pattern having peaks at about 6.2, 10.7, 12.0 and 18.9 degrees two-theta±0.2 degrees two-theta (about 150 mg) was kept in an oven at 200° C. for 30 minutes. The X-ray powder diffraction pattern of the dried crystalline pemetrexed diacid was measured.

Example 12

Preparation of Crystalline Pemetrexed Diacid Characterized by an X-Ray Powder Diffraction Pattern with Peaks at about 5.7, 12.2, 17.2 and 18.4 Degrees Two-Theta±0.2 Degrees Two-Theta Crystalline pemetrexed diacid characterized by an X-ray powder diffraction pattern having peaks at about 6.2, 10.7, 12.0 and 18.9 degrees two-theta±0.2 degrees two-theta was slurred in water (20 mL) at 50° C. for one hour, and then cooled to 26° C. over a period of about 2 hours. The suspension was then filtered. The wet solid was washed with water and dried at 40° C. under vacuum (18 mbar) for about 16 hours to afford the title compound as a light-blue solid (3.02 g) in 99.32% chemical purity (HPLC). The X-ray powder diffraction pattern of the dry material was measured and is illustrated in FIG. 8.

Example 13

Lyophilized N-[4-[2-(2-amino-4,7-dihydro-4-oxo-1H-pyrrolo[2,3-d]pyrimidin-5-yl)ethyl]benzoyll-L-glutamic acid disodium salt 5 grams of N-[4-[2-(2-amino-4,7-dihydro-4-oxo-1H-pyrrolo[2,3-d]pyrimidin-5-yl)ethyl]benzoyl]-L-glutamic acid was dissolved in 1 L of distilled water and 11.698 ml of a 2.0 M solution of sodium hydroxide was added to the solution. Mannitol (10 g) was then added to the solution and dissolved. The solution was then filtered through a bacterial filter and dried in a freeze-drier to afford 15.5 g of title compound as a white solid.

Example 14

Preparation of N-[4-[2-(2-Amino-4,7-dihydro-4-oxo-1H-pyrrolo[2,3-d]pyrimidin-5-yl)ethyllbenzoylJ-L-glutamic acid disodium salt A flask was charged with crude N-[4-[2-(2-amino-4,7-dihydro-4-oxo-1H-pyrrolo[2,3-d]pyrimidin-5-yl)ethyl]benzoyl]-L-glutamic acid (4 g), water (28 ml) and NaOH (3 equivalents) at 25° C. Complete dissolution was obtained. The pH was corrected to 10.0 with HCl1M and acetone (120 mL) was added drop wise over a period of 50 min. The obtained suspension was cooled to 2° C. in one hour, stirred at 2° C. for 10 hours and filtered. The solid was washed with acetone (30 mL) and dried at 40° C. under vacuum (18 mbar) for about 16 hours affording the title compound.

Example 15

Preparation of N-(4-[2-(2-amino-4,7-Dihydro-4-oxo-1H-Pyrrolo[2,3-d]pyrimidin-5-yl)ethyl]benzoyl)-L-Glutamic Acid Diethyl Ester p-Toluenesulfonic Acid Salt (based upon Example 6 of U.S. Pat. No. 6,262,262)

A flask is charged with 1.93 g of 4-[2-(2-amino-4,7-dihydro-4-oxo-1H-pyrrolo[2,3-d]pyrimidin-5-yl)ethyl]benzoic acid and 13.5 mL of dimethylformamide. The slurry is stirred 20 minutes and 1.94 g N-methylmorpholine is added. The mixture is cooled to 5° C. and 1.46 g chlorodimethoxytriazine is added all at once. The mixture is stirred for 1 h and then 1.99 g L-glutamic acid diethyl ester hydrochloride is added. The resulting reaction mixture is then allowed to warm to ambient temperature. The end of the reaction is detected by HPLC after about 1 h. At that point 36 mL of water and 36 mL of dichloromethane are added to the reaction mixture, which is stirred for 15 minutes. The layers are then allowed to separate. The organic phase is collected and concentrated to 13 g and then replaced by 60 mL of absolute ethanol. The solution is heated at 75° C. and 3.16g p-toluenesulfonic acid dissolved in 55 mL of ethanol absolute is added to the solution drop wise. The resulting slurry is refluxed for an hour, then cooled to ambient temperature and filtered. The wet cake is washed with 25 mL ethanol, and dried in the oven at 40° C., under vacuum overnight, to yield 3.66 g of the title compound.

What is claimed:

1. A process for preparing a pharmaceutically acceptable salt of pemetrexed diacid, comprising preparing a crystalline form of pemetrexed diacid characterized by data selected from the group consisting of
    an X-ray powder diffraction pattern having peaks at 7.7, 9.2, 16.7, and 27.4 degrees two-theta±0.2 degrees two-theta; and
    an X-ray powder diffraction pattern as depicted in FIG. 6; and converting it to a pharmaceutically acceptable salt of pemetrexed diacid.

2. A process for preparing a lyophilized form of a pharmaceutically acceptable salt of pemetrexed diacid, comprising preparing a crystalline form of pemetrexed diacid characterized by data selected from the group consisting of
    an X-ray powder diffraction pattern having peaks at 7.7, 9.2, 16.7, and 27.4 degrees two-theta±0.2 degrees two-theta; and
    an X-ray powder diffraction pattern as depicted in FIG. 6; and transforming it to a lyophilized form of a pharmaceutically acceptable salt of pemetrexed diacid.

3. The process according to claim 1, wherein the pharmaceutically acceptable salt of pemetrexed diacid is pemetrexed disodium.

4. The process according to claim 2, wherein the pharmaceutically acceptable salt of pemetrexed diacid is pemetrexed disodium.

* * * * *